United States Patent
Ralls et al.

(10) Patent No.: US 6,599,691 B1
(45) Date of Patent: Jul. 29, 2003

(54) **RAPID IMMUNOASSAY TO DETECT INFECTION WITH *MYCOBACTERIUM TUBERCULOSIS***

(75) Inventors: Stephen Alden Ralls, McLean, VA (US); Lloyd Grant Simonson, Spring Grove, IL (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 09/044,214

(22) Filed: Feb. 24, 1997

Related U.S. Application Data

(63) Continuation-in-part of application No. 08/562,772, filed on Nov. 27, 1995, now abandoned.

(51) Int. Cl.[7] ................................................. C12Q 1/00
(52) U.S. Cl. ................. 435/4; 435/5; 435/7.7; 435/7.22; 435/7.92; 435/863; 435/975; 435/7.1; 435/7.9
(58) Field of Search ........................ 435/4, 5, 7.7, 7.22, 435/7.1, 7.92, 863, 975, 7.9

(56) References Cited

U.S. PATENT DOCUMENTS 4,962,023 A  * 10/1990  Todd et al. ..................... 435/7
4,965,192 A  * 10/1990  Maes ............................. 435/7

FOREIGN PATENT DOCUMENTS

WO          9528642       * 10/1995

OTHER PUBLICATIONS

Archetti et al. J. Clin Microbiol. Jan. 1995. 33(1):79–84.*

* cited by examiner

*Primary Examiner*—Jennifer E. Graser
(74) *Attorney, Agent, or Firm*—Joseph K. Hemby, Jr.; A. David Spevack

(57) ABSTRACT

A rapid, non-invasive, semi-quantitative immunoassay of saliva has been developed to aid in the diagnosis of diseases, e.g., using saliva to detect subjects actively or previously infected with *Mycobacterium tuberculosis*, a causative organism of tuberculosis. The semi-quantitative assay comprises spotting disease-related antigens on the surface of a solid substrate; contacting the solid substrate with a saliva sample which, in positive subjects, contains primary antibodies to the disease-related antigens; contacting the primary antibodies with a label capable of being detected; and detecting and reading the label whereby exposure to the antigens is determined. The device for conducting these assays is a frame or support which holds a solid substrate capable of immobilizing the antigens of interest while permitting drainage of other materials or fluids away from the immobilized antigens. A less rapid, quantitative assay has also been developed by adapting the rapid, semi-quantitative assay to an enzyme linked immunosorbant assay thereby providing a quantitative assay capable of assessing multiple saliva samples simultaneously.

14 Claims, 1 Drawing Sheet

RAPID IMMUNOASSAY TO DETECT INFECTION WITH MYCOBACTERIUM TUBERCULOSIS

RELATED APPLICATIONS

This application is a Continuation-in-part of application Ser. No. 08/562,772 filed Nov. 27, 1995, now abandoned.

BACKGROUND OF THE INVENTION

1. Field of the Invention

This invention relates to a rapid immunoassay kit and method for semi-quantitatively detecting antibodies in human saliva to antigens of disease-related microorganisms, e.g., antibodies to *Mycobacterium tuberculosis*. This invention also encompasses an alternative embodiment that permits quantitative, though less rapid, detection of antibodies in saliva by adapting the methodology of the semi-quantitative immunoassay to an enzyme linked immunosorbant assay (ELISA). Within this invention, this alternative embodiment is referred to as the quantitative immunoassay, or similar, to distinguish it from the rapid, semi-quantitative immunoassay.

2. Description of the Prior Art

Though not substantially related to the invention described herein, there have been several efforts of peripheral interest. Ebersole has described a SEROLOGICAL METHOD FOR THE IDENTIFICATION OF MICROORGANISMS in U.S. Pat. No. 4,458,014 for the identification of diseases of the mouth. Chen et al. have described in U.S. Pat. No. 4,866,167 a DETECTION OF HUMAN ORAL CELLS BY NUCLEIC ACID HYBRIDIZATION to detect oral bacterial species. The methods of both Ebersole and Chen et al. are technically complex, time consuming, not rapid and are not based on detecting antibodies in saliva to antigens of disease-related microorganisms.

Olson et al. have described an IMMUNOLOGICAL COLOR CHANGE TEST INVOLVING TWO DIFFERENTLY COLORED REAGENT SPOTS in U.S. Pat. No. 4,639,419. Their patent describes a substantially different methodology than that described herein. This test is an agglutination reaction directed toward identifying antigenic material wherein a colored substrate and colored reagent combine, in positive reactions, to give the appearance of a third color.

Higerd and Goust have described an IMMUNOSUPPRESSIVE EXTRACELLULAR PRODUCT FROM ORAL BACTERIA in U.S. Pat. No. 4,268,434. Their patent relates to a method of producing an extracellular immunosuppressive bacterial material from various bacteria to suppress the natural immunity in patients where this outcome is desired, e.g., organ transplant patients. This procedure has substantially different objectives and methodology than the invention described herein.

Antibodies are naturally produced biomolecules which react specifically with usually foreign biomolecules called antigens. Disease-related microbial infections, e.g., *Mycobacterium tuberculosis* which causes tuberculosis, are usually characterized by the production of antibodies to the specific antigens of disease-related microorganisms. Antibodies are also produced with other diseases and afflictions, e.g., autoimmune diseases where there is an often destructive antibody response to the host—not necessarily related to a microbial antigen. In the case of autoimmune diseases, the host usually supplies the antigens of disease-related microorganisms. Within this invention, the term "disease-related antigens" includes microbial antigens and other substances capable of possessing antigenic properties and which are associated with specific diseases, conditions and disorders, including infectious diseases and autoimmune diseases. Antibodies are expressed in saliva; their detection in saliva is fundamental and unique to this invention.

This invention, as an example, can determine individuals actively or previously infected with *Mycobacterium tuberculosis* and thus aid in the diagnosis of tuberculosis. *Mycobacterium tuberculosis* causes tuberculosis (1–4) and this is widely acknowledged throughout the medical community. There are several screening tests for tuberculosis. The Mantoux test uses tuberculin purified protein derivative (PPD) which is injected intracutaneously (e.g., Tubersol®, Connaught Laboratories Limited, Willowdale, Ontario, Canada) (1). A delayed hypersensitivity reaction develops in individuals having previous infection with *Mycobacterium tuberculosis*. The injection site is normally read within 48 to 72 hours after intracutaneous injection of the antigen; a palpable induration measuring 10 mm in diameter or more is considered a positive reaction. This procedure is accepted as an aid in the diagnosis of tuberculosis infection.

The Heaf test uses a multiple puncture disk which introduces needles through concentrated Old Tuberculin applied to the skin (1). The tine test uses tuberculin adhering to metal tines; inoculation is accomplished by simple pressure into the skin (1). The Heaf and tine tests are acceptable for screening but should be confirmed by the Mantoux test (1). Antigenic material can also be applied by scratch, i.e., Pirquet's test (2). Similar to the Mantoux test, these tests generally require 48 to 72 hours after inoculation before results can be determined. The Bacillus of Caimette and Guerin (BCG) is a live, attenuated strain of *Mycobacterium bovis* which has been used with varying success as a vaccine against tuberculosis in countries where the prevalence of tuberculosis is high (5). *Mycobacterium bovis* is not normally found in humans, but since it shares antigens present in *Mycobacterium tuberculosis*, it can serve as an antigen source to detect host antibodies to *Mycobacterium tuberculosis*. BCG causes tuberculin conversion to positive; it has also been used to stimulate the immune system against a variety of medical conditions. In this invention, both PPD and BCG can serve as suitable antigens to detect host antibodies to desired mycobacteria.

Other antigens have been described. Maes has described A60-ANTIGEN FROM MYCOBACTERIA AND USE THEREOF AS TUBERCULIN VACCINE in U.S. Pat. No. 4,965,192. This patent describes the A60-antigen as effective for detecting prior exposure of an individual to mycobacterial infections through the use of a cutaneous test. This patent is similar to other inoculation tests mentioned earlier except that a new antigen is used and 24 to 48 hours are required to observe the responses at the test site.

*Mycobacterium tuberculosis* whole cells (inactivated), lipoarabinomannan of *Mycobacterium tuberculosis* (6–8) and other mycobacterial derivatives can serve as antigen sources to detect host antibodies to mycobacteria in this invention.

To continue with the *Mycobacterium tuberculosis* example of this invention, a major advantage is that tuberculosis screening can be done rapidly—in approximately 5 minutes—in one visit and in a non-invasive manner. The advantages of this invention are significant when compared with earlier tests that are invasive, take 48 to 72 hours to obtain results and require two visits of the subject, e.g., the Mantoux and other tuberculosis screening tests. These earlier tests are considered too slow and are invasive. Similar limitations apply to other medical screening and diagnostic tests that are not rapid, invasive (e.g., require blood or serum samples) or involve culturing or other complicated and expensive laboratory procedures. The premise of this use of the assay is that individuals infected with *Mycobacterium tuberculosis* develop antibodies to this bacterial species which are present in their saliva and which react with mycobacterial antigens. The antibodies are then labeled and color development detected and read visually after addition of an appropriate enzymatic substrate, if required. Color development signifies positive individuals and permits semi-quantitative assessment of antibody levels. Active or previous infection with *Mycobacterium tuberculosis* is, therefore, determined. This assay aids in the diagnosis of tuberculosis and is rapid, non-invasive, uncomplicated and inexpensive. Less rapid but quantitative simultaneous assessment of multiple (or single) saliva samples is accomplished by adapting the semi-quantitative assay to an ELISA.

What is needed is a rapid, simple, non-invasive assay to semi-quantitatively detect antibodies in saliva to antigens of disease-related microorganisms, e.g., antibodies to *Mycobacterium tuberculosis* that react with mycobacterial antigens. This assay uses human saliva, is non-invasive, can be developed and read in less than an hour, preferably in about 5 minutes, and is technically simple to operate. A rapid immunoassay to semi-quantitatively detect antibodies in saliva to antigens of disease-related microorganisms, is unique and has never been reported.

What is also needed is an immunoassay capable of quantitatively assessing multiple saliva samples simultaneously. A quantitative immunoassay is needed in instances where specific quantitative measurements or the ability to assess multiple samples simultaneously are desired over the need for a more rapid, semi-quantitative assessment. The adaptation of the rapid, semi-quantitative assay to an ELISA to quantitatively assess a single saliva sample or multiple saliva samples simultaneously is unique and has never been reported.

SUMMARY OF THE INVENTION

Accordingly, an object of this invention is an immunodiagnostic assay kit and method to rapidly and semi-quantitatively detect antibodies in saliva produced as part of an immunological response to specific, antigens of disease-related microorganisms, i.e., a host antibody response.

An additional object of this invention is a device for conducting the rapid and semi-quantitative inmmunoassay.

A further object of this invention is the adaptation of the rapid immunoassay to an ELISA permitting simultaneous, quantitative detection of antibodies in multiple (or single) saliva samples produced as part of an immunological response to specific disease-related antigens, i.e., a host antibody response.

These and additional objects of the invention are accomplished by an immunoassay kit and method for rapidly and semi-quantitatively detecting antibodies in saliva to antigens of disease-related microorganisms, and by adaptation of the rapid, semi-quantitative immunoassay to an ELISA thereby permitting quantitative assessment of a single saliva sample or simultaneous quantitative assessment of multiple saliva samples. With this invention, the semi-quantitative assay can be performed on an aliquot of a saliva sample. The semi-quantitative assessment can then be extended by using the quantitative assay to assess a different aliquot of the same saliva sample.

Antigens of disease-related microorganisms are immobilized on a solid substrate and contacted with a saliva sample from the human subject being tested. The saliva samples are filtered with a sample filter or treated with some other separating device such as a centrifuge prior to their contact with the immobilized antigens. Antibodies to the antigens may be present in the saliva sample. These primary antibodies, if present, bind to the immobilized antigens. After blocking, the primary antibodies are then contacted typically with secondary antibodies specific for the primary antibodies having a label or indicator capable of being detected, e.g., alkaline phosphatase. Secondary antibodies can be anti-human IgG, IgA, IgM, alone or in combination. After the addition of an appropriate enzymatic substrate, if required, the label develops identifying the presence of the antibodies whereby active or previous infection with the antigen, e.g., *Mycobacterium tuberculosis*, is determined. The device for conducting the semi-quantitative assay is a frame or support which holds a solid substrate capable of immobilizing the antigens of interest while permitting drainage of other materials or fluids away from the bound antigens. The device for the quantitative assay includes an ELISA plate reader, 96-well plates, a plate washer, a multidrop dispenser, and related ELISA equipment. The 96-well plates, or similar, are capable of immobilizing the desired antigens of disease-related microorganisms thereby allowing the fundamental immunologic reaction of the semi-quantitative assay to take place in the wells of the plates and measured quantitatively with the ELISA plate reader. For the quantitative assay, each well of the 96-well plates serves as a solid substrate capable of immobilizing the desired antigens of disease-related microorganisms.

BRIEF DESCRIPTION OF THE DRAWING

A more complete appreciation of the invention will be readily obtained by reference to the following Description of the Preferred Embodiments and the accompanying drawing. A more complete appreciation of the invention will be readily obtained by reference to the following Description of the Preferred Embodiments and the accompanying drawings. The representation in each of the figures is diagrammatic and no attempt is made to indicate actual scales or precise ratios. Proportional relationships are shown as approximations.

Figure 1:
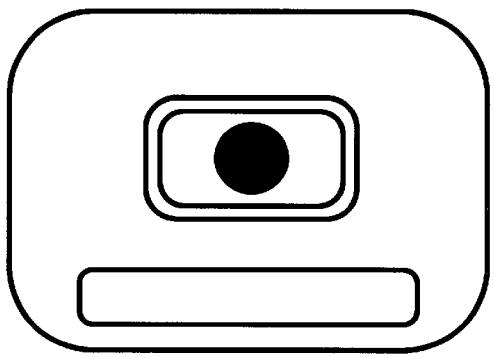
FIG. 1 is an embodiment of the device for the rapid, semi-quantitative assay and illustrates a positive reaction and the presence of antibodies in human saliva to mycobacterial antigens, thereby normally reflecting active or previous infection with *Mycobacterium tuberculosis*.
Figure 2:
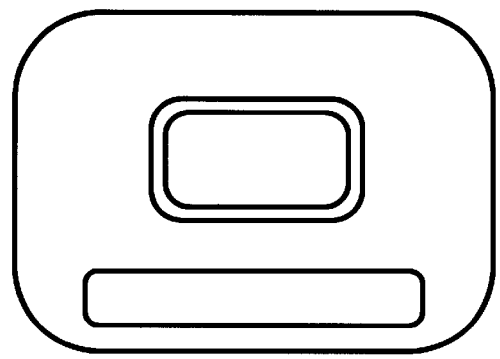
FIG. 2 is an embodiment of the device for the rapid, semi-quantitative assay and illustrates a negative reaction and the absence of antibodies in human saliva to mycobacterial antigens, thereby normally reflecting no active or previous infection with *Mycobacterium tuberculosis*.

The less rapid, quantitative assay uses conventional ELISA equipment and materials and cannot, therefore, be suitably rendered in a figure.

DESCRIPTION OF THE PREFERRED EMBODIMENTS

The lack of rapid, accurate, non-invasive diagnostic screening methods for many medical conditions unnecessarily increases subject risk, contributes to inefficiency, and often increases costs. For example, tuberculosis continues to pose a serious health problem worldwide and screening personnel for tuberculosis is routinely included in most immunization programs and physical examinations. This invention allows rapid, one-visit identification of subjects actively or previously infected with *Mycobacterium tuberculosis*, the bacterial species responsible for tuberculosis, by semi-quantitative assessment of *Mycobacterium tuberculosis* antibodies in saliva samples from the subjects. Within this invention, the terms "infected" and "infection" refer to exposure (active or previous) to an infectious.microorganism (in this example, *Mycobacterium tuberculosis*) sufficient to elicit a detectable host antibody response to the microorganism. This invention also allows identification of similarly infected subjects through a quantitative, tho ugh less rapid, assessment of antibodies in saliva by adapting the methodology of the semi-quantitative immunoassay to an ELISA. The quantitative immunoassay thereby permits simultaneous quantitative detection of antibodies to *Mycobacterium tuberculosis* in saliva samples of multiple (or single) subjects.

The invention is a new and unique approach to aid in diagnostic screening. The invention is directed to immunodiagnostic assays to detect antibodies in saliva to antigens of disease-related microorganisms. For example the presence of certain levels of antibodies to *Mycobacterium tuberculosis* in saliva normally indicates active or previous infection with *Mycobacterium tuberculosis*. With the semi-quantitative assay, the invention is intended for one-visit screening applications to aid in the diagnosis of tuberculosis and is a significant improvement over earlier methods which require 48 to 72 hours and a follow-up visit to obtain results. With its adaptation to an ELISA, the invention can simultaneously assess multiple saliva samples of subjects and provide quantitative measurements of the desired antibodies in about 6 to 8 hours which is considerably faster than earlier methods.

This rapid assay kit and method are designed to detect semi-quantitatively the presence of antibodies to antigens of disease-related microorganisms in human saliva, e.g., antibodies to *Mycobacterium tuberculosis* that react with certain mycobacterial antigens. The assay is fully developed and readable in under an hour, usually about 5 minutes, from the time the subject's saliva sample is contacted with the solid substrate. In a preferred commercial embodiment, the antigens are immobilized on the solid substrate in advance. Within this invention, the terms "rapid assay" and "rapid immunoassay" mean an assay or test that can be developed in under an hour, preferably in less than one-half hour. Most preferably, this rapid assay is fully readable in approximately 5 minutes from the application of the subject's saliva sample to the solid substrate. The kit and method are technically easy to use.

In general, a preferred embodiment of the invention is a clinical diagnostic kit and method designed to rapidly detect the presence of antibodies in saliva that are specific to a disease. For example, the assay uses mycobacterial antigens, e.g., tuberculin BCG antigens, that react with and allow semi-quantitative detection of antibodies to *Mycobacterium tuberculosis* that may be present in saliva. The kit and method first comprise immobilizing the desired, antigens on the solid substrate and pre-blocking the remainder of the solid substrate; in a preferred commercial embodiment, antigen immobilization and pre-blocking are done in advance. A stimulated saliva sample suspected of containing antibodies to the antigens of disease-related microorganisms is then obtained from the subject being tested. The stimulated saliva sample can be gathered by any of the known techniques for gathering stimulated saliva samples. Saliva is stimulated by chewing paraffin, sugarless chewing gum, or similar. Saliva samples are typically filtered with a sample filter (Whatman part no. AV125UGMF, autovial disposable syringeless filter glass microfiber, 0.45 $\mu$m; from Fisher, catalog no. 09-919) to remove undesired particulate matter. Alternatively, samples are treated with some other suitable separating device, e.g., samples can be centrifuged in a high-speed microcentrifuge for 5 minutes (or more). Saliva samples are then normally diluted 1:1 with physiologic saline. An aliquot of the diluted saliva sample is placed on a solid substrate, preferably a flow-through filter type device (e.g., Devaron, Inc., Dayton, N.J., 0.45 $\mu$m or 0.60 $\mu$m) or a device such as described by Oprandy in U.S. Pat. No. 5,039,493 or some other antigen-immobilizing device. The antibodies in the saliva, if present, react with the antigens of disease-related microorganisms. The solid substrate is then blocked and washed. The solid substrate can be any of the commonly used solid substrates such as nitrocellulose filter media, any of the materials described by Oprandy or some other antigen-immobilizing device. Once the antigens are imimobilized on the solid substrate, the solid substrate is contacted with the saliva sample containing, if positive, antibodies that are specific for the immobilized antigens (e.g., antibodies in saliva to *Mycobacterium tuberculosis* that react with the immobilized mycobacterial antigens). The antibodies are then contacted with a label capable of being detected, thereby identifying the presence of the antibodies. Any detectable label or indicator can be used such as an enzyme (e.g., alkaline phosphatase; peroxidase; galactosidase; etc.) which reacts with an appropriate enzymatic substrate to yield an insoluble end product. Labels such as colloidal gold coupled to protein-A, protein-G, or some other protein can also be used. Other suitable detectable labels include fluorescent markers, radionuclides, latex particles and others. Once labeled, the amount of desired antibodies in the sample can be semi-quantified by detecting the relative strength of the color development produced by the labeling process. Also, the use of colloidal gold or other labels such as enzymes or fluorochromes can be attached to several probes such as protein-A, protein-G, goat anti-rabbit IgG, goat anti-mouse IgG, and others.

A principal alternative embodiment adapts key elements of the rapid immunoassay to an ELISA for quantitative assessment of a single saliva sample or simultaneous quantitative assessment of multiple saliva samples. This embodiment is normally a laboratory procedure requiring ELISA laboratory equipment and materials and, therefore, is not considered rapid as the term is used herein. This embodiment, though less rapid, has the advantage of quantitative measurements as opposed to the semi-quantitative assessment of saliva samples using the rapid immunoassay. This quantitative assay typically takes about 6 to 8 hours for a fully developed quantitative reading which is, nevertheless, considerably faster than commercially available alternatives taking 48 to 72 hours. The quantitative assay can also be used to extend the assessment of the semi-quantitative assay by using different aliquots of the same saliva sample in both assays.

A further alternative embodiment applies the unique basis of this invention, i.e., detecting antibodies in saliva to antigens of disease-related microorganisms, to all diseases that are associated with detectable host antibodies to antigens of disease-related microorganisms, i.e., any disease, condition or disorder having a detectable host antibody response.

Having described the invention, the following two examples are given to illustrate specific applications of the invention for detecting subjects actively or previously infected with organisms causative of tuberculosis, including the best.mode now known to perform the invention. Example 1 describes the semi-quantitative immunoassay for rapidly detecting antibodies in saliva to *Mycobacterium tuberculosis*. Example 2 describes the less rapid, quantitative immunoassay for simultaneously detecting antibodies to *Mycobacterium tuberculosis* in multiple (or single) saliva samples. These specific examples are not intended to limit the scope of the invention described in this application.

EXAMPLE 1

A rapid immunoassay to semi-quantitatively detect antibodies to mycobacterial antigens, normally *Mycobacterium tuberculosis* in humans, is described in 10 simple and rapid steps:

1. A Bacillus of Calmette and Guerin (BCG) antigen preparation is made with an ampule of BCG Vaccine U.S.P. (FSN 6505-01-337-3126, Organon Technika Corp., Durham, N.C.). The ampule is broken and the contents rehydrated with 0.5 ml of carbonate coating buffer, pH 9.6. The ampule contains $1–8\times10^8$ colony forming units (cfu) of the BCG antigen, 50 mg per 0.5 ml (or 100 mg per ml). The ampule contents are heat inactivated at 56° C. for 1 hour. The contents are then diluted 1:1 with a solution of MonoPure Elution Buffer (catalog no. 1851520, lot no. 870127087, Pierce Chemical Co., Rockford, Ill.) with 1% Tween-20 (no. 170-6531, Bio-Rad Labs) mixed 1:1 with 2 M sodium acetate buffer, pH 8.0. The mixture is centrifuged in a high-speed microcentrifuge (10,000 rpm Eppendorf) for 5 minutes, the supernatant removed, and the antigen pellet rehydrated with 1 ml of phosphate-buffered saline (PBS). After suitable pre-blocking (see step 2), 1.5 µl of the BCG antigen preparation are then spotted onto a solid substrate, i.e., a flow-through filter device (Devaron, Dayton, N.J., 0.45 em). The carbonate coating buffer, pH 9.6, is prepared as follows:

Coating Buffer, pH 9.6, 1 L

| | |
|---|---|
| Ultrapure Water | 1000 ml |
| $Na_2CO_3$ | 1.59 g |
| $NaHCO_3$ | 2.93 g |
| $NaN_3$ | 0.2 g |

An alternative antigen source uses tuberculin purified protein derivative (PPD) (FSN 6505-00-105-0102, Tubersol®, Connaught Laboratories Ltd., Willowdale, Ontario, Canada). One vial of this PPD source (labeled as 5 ml, actually 8 ml) is dialyzed against deionized water for 1.25 hours, then dialyzed against tris buffered saline, pH 9.55, for 2 hours in 3,500 molecular weight dialysis tubing. The final volume is 9.5 ml. The solution is next freeze-dried and rehydrated with 800 µl of carbonate coating buffer, pH 9.6 (10×Dialyzed PPD). Similar to above, 1.5 µl are then spotted onto a flow-through filter device (Devaron, Dayton, N.J., 0.45 µm) that has not been pre-blocked. Two other alternate antigen sources are *Mycobacterium tuberculosis* whole cells (inactivated) and Mycobacterium lipoarabinomannan.

2. Nonspecific binding to the solid substrate filter surface is reduced by adding 4 drops (160 µl) of 0.05% gelatin (catalog no. G-8, 275 Bloom; lot no. 734286, Type A purified grade CAS reg. 9000-70-8, Fisher Scientific Co.) plus 0.05% skim milk, dehydrated (Difco, no. 0032-01, control no. 704524) in PBS. It is heated to 56° C. overnight, about 18 hours. One (1) liter of PBS, pH 7.4, is prepared as follows:

PBS, pH 7.4, 1 L

Ultrapure Water 1000 ml

| | |
|---|---|
| NaCl | 8.0 g |
| $KH_2PO_4$ | 0.2 g |
| $Na_2HPO_4.12H_2O$ | 2.9 g |
| KCl | 0.2 g |
| $NaN_3$ (Sodium Azide) | 0.2 g |

3. The solid substrate filter surface is then washed with one drop (50 µl) of the solution outlined in step 2 to which 0.05% Tween-20. (no. 170-6531, Bio-Rad Labs) has been added to a concentration of 0.5 ml/L.

4. A sugarless chewing gum or paraffin-stimulated saliva sample from a human subject is filtered through a sample filter (Whatman part no. AV125UGMF, autovial disposable syringeless filter glass microfiber, 0.45 µm; from Fisher, catalog no. 09-919). Alternatively, some other suitable separating device is used, e.g., samples can be centrifuged in a high-speed microcentrifuge for 5 minutes. Accepted safety and infection control practices should be followed when working with subject samples, including wearing gloves and safety glasses. Three (3) drops (120 µl) of the saliva filtrate are then mixed 1:1 with 3 drops (120 µl) of sterile 0.85% NaCl by shaking for 10 seconds. Two (2) drops (80 µl) of this mixture are then added to the filter surface of the flow-through filter device (i.e., the solid substrate filter surface) equivalent to 1 drop, 40 µl, of undiluted saliva.

5. The solid substrate filter surface is washed again as in step 3.

6. One (1) drop of 10% normal goat serum (catalog no. 200-6210AG, control no. 34N1903, Gibco, Grand Island, N.Y.) in PBS is then added to the solid substrate filter surface. The serum is earlier heated at 56° C. for 1 hour prior to its dilution with PBS.

7. A detecting antibody solution is prepared using goat anti-human IgG heavy and light chains, alkaline phosphatase labeled antibody conjugate (KPL catalog no. 075-1006, Kirkegaard & Perry Laboratories, Inc., Gaithersburg, Md.). Alternatively, anti-human IgG, IgA, IgM, alone or in combination, can be utilized. The antibody conjugate is supplied as a powder which is rehydrated in 1 ml deionized water, then diluted 1:8 with 0.85% NaCl, then diluted 1:1 with Stabilzyme AP (catalog no. SA01-0125, lot no. SA01401, BSI Corp. Eden Prairie, Minn.). The antibody solution is, therefore, a 1:16 final dilution, and 1 drop (50 µl) is added to the solid substrate filter surface.

8. The solid substrate filter surface is washed again as in step 3.

9. Four (4) drops (200 µl) of BCIP/NBT alkaline phosphatase substrate (5-bromo-4-chloro-3-indoxyl phosphate/p-nitroblue tetrazolium system)(catalog no. ES006-500 ml, Chemicon International Inc.) to which 0.5 mg of Levamisole/ml (catalog no. L-9756; Sigma Chemical Co., St. Louis, Mo.) has been added are next added to the solid substrate filter surface for color development.

10. Two (2) drops (100 µl) of a 1:1 vol:vol mixture of 0.2 M ethylenediaminetetraacetic acid (EDTA) (no. 4653, J. T. Baker Chemical Co., Phillipsburg, N.J.) with tris buffered saline, pH 2.8, (final pH=5.17; final EDTA=0.1 M) are added to the solid substrate filter surface to arrest color development. Semi-quantitative levels of desired antibodies are determined visually by reading and comparing the intensity of the color development against a standard color intensity scale (or chart). The scale is developed in advance by performing the semi-quantitative assay on known concentrations of known antibodies.

The semi-quantitative assay is usually completed in about 5 minutes from the time that the saliva sample is contacted with the filter surface of the solid substrate. In a preferred commercial embodiment, the antigen immobilization and related blocking steps are done in advance. The color changes that develop reflect semi-quantitatively the levels of salivary. antibodies to mycobacterial antigens, i.e., normally *Mycobacterium tuberculosis*, as shown in FIG. 1.

The assay does not have to be conducted in the particular order between immobilizing the antigens of disease-related microorganisms and detecting the antibodies. In a preferred commercial embodiment, the antigens of disease-related microorganisms are immobilized in advance on a solid substrate, preferably nitrocellulose media which is part of a flow-through filter device or similar. The solid substrate filter surface is then pre-blocked. The device is then packaged until needed, preferably with the materials, reagent and instructions necessary to perform the assay. When needed, the device is removed from the packaging and a suspected antibody-containing sample, e.g., human saliva, is contacted with the pre-blocked, antigen-containing, solid substrate filter surface. The solid substrate surface is then blocked and washed. An antibody label or indicator which reacts with the antibodies is then applied. When the label is alkaline phosphatase antibody solution, as prepared in step 7 of Example 1, with a BCIP/NBT enzymatic substrate system, a color will develop as shown in FIG. 1 for samples positive for certain levels of antibodies in saliva to mycobacterial antigens, normally *Mycobacterium tuberculosis* in humans. Typically, color changes are read and compared against a standard color intensity scale (or chart) thereby determining semi-quantitative levels of the desired antibodies.

EXAMPLE 2

An inmunoassay to quantitatively detect antibodies in saliva to mycobacterial antigens, normally *Mycobacterium tuberculosis* in humans, is described in 14 simple steps:

1. A sugarless chewing gum or paraffin-stimulated saliva sample is gathered from a human subject. With this quantitative assay, samples from multiple subjects can be assessed simultaneously. Each sample is filtered through a sample filter (Whatman part no. AV125UGMF, autovial disposable syringeless filter glass microfiber, 0.45 $\mu$m; from Fisher, catalog no. 09-919). Alternatively, samples are treated with some other suitable separating device, e.g., samples can be centrifuged in a high-speed microcentrifuge for 5 minutes (or more). The quantitative assay can also be used to extend the assessment of the semi-quantitative assay (an example of the semi-quantitative assay is described earlier in Example 1) by using different aliquots of the same saliva sample in both assays. Accepted safety and infection control practices should be followed when working with subject samples, including wearing gloves and safety glasses.

2. A BCG antigen preparation is made with an ampule of BCG Vaccine U.S.P. (FSN 6505-01-337-3126, Organon Technika Corp., Durham, N.C.). The ampule is broken and the contents rehydrated with 0.5 ml sterile saline (0.85%). The ampule contains 1–8×10$^8$ cfu of the BCG antigen, 50 mg per 0.5 ml (or 100 mg per ml). The contents are heat inactivated at 56° C. for 1 hour. The contents are then diluted 1:1 with a solution of MonoPure Elution Buffer (catalog no. 1851520, lot no. 870127087, Pierce Chemical Co., Rockford, Ill.) with 1% Tween-20 (no. 170-6531, Bio-Rad Labs) mixed 1:1 with 2 M sodium acetate buffer, pH 8.0. The mixture is centrifuged in a high-speed microcentrifuge (10,000 rpm Eppendorf) for 10 minutes, the supernatant removed, and the antigen pellet rehydrated with 1 ml of PBS (with sodium azide). This yields 1–8×10$^8$ cfu/ml. The rehydrated antigen pellet is mixed-by shaking vigorously. The mixed antigen pellet is then diluted 1:10 (1:20; 1:40; 1:80) in coating buffer (1X) and 100 $\mu$l of diluted antigen preparation is pipetted into each well of 96-well plates. In this example of the quantitative assay, each well of the 96-well plates serves as a solid substrate immobilizing the desired antigens. Alternate antigen sources are PPD, *Mycobacterium tuberculosis* whole cells (inactivated) and Mycobacterium lipoarabinomannan 3. The well plates are centrifuged for 15 minutes at 2,000 rpm.

4. The fluid is aspirated from the plate wells using Plate Washer EL404 and 100 $\mu$l of 0.5% glutaraldehyde-PBS (0.1 ml of 50% glutaraldehyde per 10 ml of PBS) is added to each well. The plates are incubated at room temperature for 15 minutes.

5. The plates are washed 3 times with wash solution. Two hundred (200) $\mu$l of blocking solution is added to each well. The plates are then incubated at room temperature for 30 minutes.

6. The plates are washed 3 $\mu$times with wash-solution.

7. The saliva samples are diluted 1:2 to 1:16 with sterile 0.85% NaCl. One hundred (100) $\mu$l of filtered and diluted saliva are added to each well and allowed to incubate for 1 hour at 37° C.

8. The plates are washed 3 times with wash solution.

9. One hundred (100) $\mu$l of 10% normal goat serum in PBS (with azide) is added to, each well. The wells are aspirated after 10 minutes.

10. A detecting antibody solution is prepared using goat anti-human IgG heavy and light chains, alkaline phosphatase labeled antibody conjugate (KPL catalog no. 075-1006, Kirkegaard & Perry Laboratories, Inc., Gaithersburg, Md.). Alternatively, anti-human.IgG, IgA, IgM, alone or in combination, can be utilized. The antibody conjugate is supplied as a powder which is rehydrated in 1 ml deionized water, then diluted 1:8 with 0.85% NaCl. One hundred (100) $\mu$l of the antibody solution is added to each well. The wells are diluted 1:500 in (1:1 vol:vol) PBS:Stabilzyme AP (catalog no. SA01–0125, lot no. SA01401, BSI Corp. Eden Prairie, Minn.). The plates are then incubated for 1 hour at 37° C.

11. The plates are washed 3 times with wash solution followed by 3 times with distilled water.

12. Two hundred (200) $\mu$l of alkaline phosphatase substrate (p-nitrophenyl phosphate, disodium, 5mg/tablet dissolved 5 mg/5 ml in 10% diethanolamine) are added to each well. The plates are incubated for 15 to 45 minutes in the dark at room temperature, and read at 15, 30, and 45 minutes or until sufficient yellow color appears. This alkaline phosphatase substrate reagent can be prepared using the formula for the diethanolamine in reagent instructions and nitrophenyl phosphate tablets (Sigma Chemical Co., St. Louis, Mo.) or by using a commercial kit (KPL catalog no. 508000, Kirkegaard & Perry Laboratories, Inc, Gaithersburg, Md.). The color intensity that develops in each well reflects the relative levels of desired antibodies detected.

13. The reaction is stopped using 2N NaOH at 50 $\mu$l per well.

14. Antibody levels are quantified by absorbance readings of the color changes obtained by reading the plates at 405 nm using the CERES UV900C Plate Reader. There are separate operating instructions for the Bio-Tek Instruments CERES UV900C Plate Reader, Bio-Tek Instruments EL 404 Microplate Auto Washer and Lab Systems Multidrop Dispenser. The readings normally reflect quantitative levels of antibodies to *Mycobacterium tuberculosis* in each saliva sample assayed.

Formulas for reagents include:

| PBS-0.25-BSA/Tween-20 Wash Solution, 1 L | |
|---|---|
| PBS | 1000 ml |
| Bovine Serum Albumin (BSA) | 2.5 g |
| Tween-20 | 0.5 ml |
| Coating Buffer, pH 9.6, 1 L | |
| Ultrapure Water | 1000 ml |
| $Na_2CO_3$ | 1.59 g |
| $NaHCO_3$ | 2.93 g |
| $NaN_3$ | 0.2 g |
| Glutaraldehyde 0.5% | |
| 0.1 ml of 50% solution per 10 ml of PBS | |
| Blocking Solution, 250 ml | |
| PBS | 250 ml |
| BSA | 2.5 g |
| Gelatin | 0.25 g |
| Glycine | 1.875 g |
| Skim Milk | 0.125 g |
| 0.5% BSA-1% Goat Serum PBS, 100 ml | |
| BSA | 0.5 g |
| PBS | 100 ml |
| Goat Serum | 1 ml |

The quantitative assay is usually completed in about 6 to 8 hours. The quantitative assay does not have to be conducted in the particular order between gathering the saliva sample and reading the plates to determine quantitative levels of the desired antibodies.

ADVANTAGES AND NEW FEATURES

A major advantage of this invention is that a semi-quantitative assay of disease-related antibodies in saliva (to *Mycobacterium tuberculosis* for example) can be performed and read in about 5 minutes compared typically to 2 days or longer for conventional screening. The use of saliva for the source of antibodies is also unique. This semi-quantitative assay is sensitive, specific, non-invasive and can be used in a medical treatment office or similar facility with results obtained while the subject waits. This assay saves an enormous amount of money given the cost savings associated with a subject not having to return days later to determine or receive test results. Subjects do not have to return to have a PPD test read saving the costs of the follow-up visit. In addition, in some scenarios, such as testing refugees, follow-up visits are difficult, unpredictable and not easily controlled. Costs for laboratory analysis, where applicable, can also be avoided or greatly minimized. The semi-quantitative assay also eliminates the need for use and disposal of needles for blood and serum samples and eliminates adverse reactions to intentionally-injected antigens as in the Mantoux test. The inventors are not aware of any other similar inventions or products available on the market.

A second major advantage is that the method can be adapted, when desired over a more rapid semi-quantitative assessment, to an ELISA thereby providing simultaneous quantitative assays of multiple (or single if desired) saliva samples. Like the semi-quantitative assay, the quantitative assay is non-invasive and also eliminates the need for use and disposal of needles for blood and serum samples and eliminates adverse reactions to intentionally-injected antigens as in the Mantoux test. The quantitative assay, though less rapid than the semi-quantitative assay, is, nevertheless, faster than commercially available tests requiring 48 to 72 hours such as the PPD. The inventors are unaware of any similar quantitative assay that measures salivary antibodies to disease-related antigens.

PUBLICATIONS

1. Holvey, David N. and Talbott, John H. (eds.). *The Merck Manual of Diagnosis and Therapy*. Rahway, N.J.: Merck Sharp & Dohme Research Laboratories, 12th ed., 1972, pp. 136, 141–142.

2. Berkow, Robert and Fletcher, Andrew J. (eds.). *The Merck Manual of Diagnosis and Therapy*. Rahway, N.J.: Merck Sharp & Dohme Research Laboratories, 15th ed., 1987, pp. 113–116.

3. Isselbacher, Kurt J., Braunwald, Eugene, Wilson, Jean D., Martin, Joseph B., Fauci, Anthony S. and Kasper, Dennis L. *Harrison's Principles of Internal Medicine*. New York, NY: McGraw-Hill, Inc., vol. 1, 13th ed., 1994, pp. 710–718.

4. Schroeder, Steven A., Tiernery, Jr. Lawrence M., McPhee, Stephen J., Papadakis, Maxine, A. and Krupp, Marcus A. *Current Medical Diagnosis & Treatment*. Norwalk, Conn.: Appleton & Lange, 1992, pp. 207–213.

5. Baron, Ellen J., Chang, Robert S., Howard, Dexter H., Miller, James N. and Turner, Jerrold A. *Medical Microbiology. A Short Course*. New York, N.Y.: Wiley-Liss, Inc., 1994, pp. 415–416.

6. Chattedjee, D., Hunter, S. W., McNeil, M. and Brennen, P. J. Lipoarabinomannan. Multiglycosylated form of the mycobacterial mannosylphosphatidylinositols. J. Biol. Chem. 1992; 267(9):6228–33.

7. Chatterjee, D., Lowell, K., Rivoire, B., McNeil, MR. and Brennen, P. J. Lipoarabinomannan of *Mycobacterium tuberculosis*. Capping with mannosyl residues in some strains. J. Biol. Chem. 1992; 267(9):6234–39.

8. Khoo, K. H., Douglas, E., Azadi, P., Inamine, J. M. et al. Truncated structural variants of lipoarabinomannan in ethambutol drug-resistant strains of *Mycobacterium smegmatis*. Inhibition of arabinan biosynthesis by ethambutol. J. Biol. Chem. 1996; 271(45):28682–90.

Obviously, many modifications and variations of the present invention are possible in light of the above teaching. Therefore, it is to be understood that, within the scope of the appended claims, the invention may be practiced otherwise than as specifically described. The principles described above can be readily modified or adapted for various applications without departing from the generic coricept, and, therefore, such adaptations and modifications are intended to be comprehended within the meaning and range of equivalents of the enclosed embodiments. It is to be understood that the terminology and phraseology herein are for the purpose of description and not of limitation.

What is claimed is:

1. An immunodiagnostic assay kit for detecting semi-quantitatively in about five (5) minutes or quantitatively in about six (6) to eight (8) hours antibodies in saliva specific to a disease comprising:

antigens specific to a disease to be identified immobilized on a solid flow-through substrate by spotting or non-specific contact;

a blocking agent for application over the antigen on said solid substrate capable of reducing nonspecific binding;

a filter to remove particulate matter from a saliva sample suspected of containing primary antibodies specific to said antigens;

secondary antibodies specific to said primary antibodies available for use; and a label or indicator capable of attaching directly to the primary antibodies or indirectly to said secondary antibodies producing a detectable signal.

2. The kit of claim 1 wherein the disease is any disease, condition or disorder having a detectable and specific antibody that is present or remains in saliva said antibody responding to a disease related antigen.

3. The kit of claim 2 wherein the disease is tuberculosis.

4. The kit of claim 3 wherein the microorganisms having antigens specific to a disease are selected from the group consisting of mycobacteria and derivatives, *Mycobacterium tuberculosis, Mycbacterium bovis*, tuberculin purified protein derivative, the Bacillus of Calmette and Guerin and lipoarabinomannan of *Mycobacterium tuberculosis*.

5. The kit of claim 1 wherein the label or indicator is selected from the group consisting of colloidal gold; colloidal gold coupled to a protein; an enzyme; a fluorescent marker; a radionuclide; and latex particles.

6. The kit of claim 5 wherein the label is alkaline phosphatase.

7. The kit of claim 5 wherein the protein coupled to the colloidal gold is selected from the group consisting of protein-A and protein-G.

8. An immunodiagnostic assay method for detecting antibodies in saliva specific to a disease comprising:

contacting and immobilizing antigens specific to a disease with a solid flow-through substrate to form a spot or as nonspecific contact;

blocking said solid substrate to reduce nonspecific binding;

gathering a saliva sample suspected of containing primary antibodies to the antigens specific to a disease;

separating particulate matter from said sample with a separating device selected from the group consisting of filters and centrifuges to form a salivary sample filtrate or supernatant;

spotting the saliva filtrate or supernatant on to the immobilized antigen on the solid substrate;

contacting the immobilized antigen and sample on the solid substrate with a label capable of directly attaching to the primary antibodies or indirectly attaching to secondary antibodies specific to the primary antibodies; and detecting and reading the intensity of the label in less than 5 minutes whereby the presence and concentration of primary antibodies in the sample are determined.

9. The method of claim 8 wherein the disease is any disease, condition or disorder having a specific, detectable host antibody response.

10. The method of claim 9 wherein the disease is tuberculosis.

11. The method of claim 10 wherein the microorganisms containing antigens specific to a disease are selected from the group consisting of mycobacteria and derivatives, *Mycobacterium tuberculosis, Mycobacterium bovis*, tuberculin purified protein derivative, the Bacillus of Calmette and Guerin and lipoarabinomannan of *Mycobacterium tuberculosis*.

12. The method of claim 8 wherein the label or indicator is selected from the group consisting of colloidal gold; colloidal gold coupled to a protein; an enzyme; a fluorescent marker; a radionuclide; and latex particles.

13. The method of claim 12 wherein the label is alkaline phosphatase.

14. The method of claim 12 wherein the protein coupled to the colloidal gold is selected from the group consisting of protein-A and protein-G.

* * * * *